United States Patent
Hund et al.

(10) Patent No.: US 9,764,098 B2
(45) Date of Patent: Sep. 19, 2017

(54) ATTACHMENT FOR A SYRINGE OR CARPULE

(71) Applicant: Vetter Pharma-Fertigung GmbH & Co. KG, Ravensburg (DE)

(72) Inventors: Petra Hund, Berg (DE); Jochen Zenker, Ravensburg (DE)

(73) Assignee: Vetter Pharma-Fertigung GmbH & Co. KG, Ravensburg (DE)

( * ) Notice: Subject to any disclaimer, the term of this patent is extended or adjusted under 35 U.S.C. 154(b) by 181 days.

(21) Appl. No.: 14/713,191

(22) Filed: May 15, 2015

(65) Prior Publication Data

US 2015/0246184 A1 Sep. 3, 2015

Related U.S. Application Data

(63) Continuation of application No. PCT/EP2013/073621, filed on Nov. 12, 2013.

(30) Foreign Application Priority Data

Nov. 15, 2012 (DE) .................. 10 2012 022 359

(51) Int. Cl.
- *A61M 39/10* (2006.01)
- *A61M 5/34* (2006.01)
- *A61M 5/24* (2006.01)

(52) U.S. Cl.
CPC ............ *A61M 5/343* (2013.01); *A61M 5/344* (2013.01); *A61M 5/345* (2013.01); *A61M 2005/2437* (2013.01)

(58) Field of Classification Search
CPC .............. A61M 39/1011; A61M 39/10; A61M 2039/1077; A61M 2005/3104; A61M 5/345

(Continued)

(56) References Cited

U.S. PATENT DOCUMENTS 5,702,374 A * 12/1997 Johnson ................ A61M 39/10
128/912
2006/0163515 A1* 7/2006 Ruschke ............... A61M 39/26
251/149.7

(Continued)

FOREIGN PATENT DOCUMENTS

| DE | 102009007250 | 7/2010 |
| DE | 102011013791 | 9/2010 |

(Continued)

OTHER PUBLICATIONS

International Search Report of corresponding International Application No. PCT/EP2013/073621, mailed on Jan. 31, 2014.

(Continued)

*Primary Examiner* — Gerald Landry, II
(74) *Attorney, Agent, or Firm* — Edell, Shapiro & Finnan LLC

(57) ABSTRACT

An attachment for a syringe, carpule, or the like, includes a distal end and a terminal extension with an outer surface, a free end, and a depression introduced at a spacing into the outer surface. The attachment includes an annular base body and is placeable onto the extension. The base body encloses a free space into which the extension is introducible. The base body contains two materials a first material which is dimensionally stable and a second material which is softer than the first material and deformable. The base body has an engagement region, which engages into the depression. The extension is thus characterized in that the base body has, along an imaginary circumferential line, a first region with the first material and a second region containing the second material. The second material deforms into the depression in a placed-onto-the-extension state. The second material is embedded into the first material.

12 Claims, 7 Drawing Sheets

(58) Field of Classification Search
USPC ... 604/164.07, 192, 240, 243, 533, 535, 905
See application file for complete search history.

(56) References Cited

U.S. PATENT DOCUMENTS

| | | | |
|---|---|---|---|
| 2006/0178627 A1* | 8/2006 | Geiger | A61M 5/3134 604/111 |
| 2007/0129591 A1* | 6/2007 | Yanke | A61M 5/1785 588/16 |
| 2007/0219508 A1* | 9/2007 | Bisegna | A61M 5/31513 604/218 |
| 2010/0007134 A1* | 1/2010 | Elton | A61M 39/10 285/31 |
| 2011/0282295 A1* | 11/2011 | Pupke | A61M 5/347 604/187 |
| 2011/0282302 A1* | 11/2011 | Lopez | A61M 39/10 604/247 |
| 2012/0130351 A1* | 5/2012 | Alvain | A61M 5/347 604/533 |
| 2012/0179108 A1* | 7/2012 | Delabie | A61M 5/347 604/187 |
| 2012/0191037 A1* | 7/2012 | Patel | F16K 5/0407 604/30 |
| 2013/0046287 A1* | 2/2013 | Davis | A61M 39/10 604/535 |
| 2014/0012204 A1* | 1/2014 | Bosshardt | A61M 39/1011 604/187 |
| 2014/0171875 A1* | 6/2014 | Poncon | A61M 5/344 604/192 |

FOREIGN PATENT DOCUMENTS

| | | |
|---|---|---|
| EP | 1099450 | 5/2001 |
| EP | 1502616 | 2/2005 |
| WO | 2012116790 | 9/2012 |

OTHER PUBLICATIONS

English language International Preliminary Report on Patentability and Written Opinion for International Patent Application No. PCT/EP2013/073621.

\* cited by examiner

ATTACHMENT FOR A SYRINGE OR CARPULE

CROSS REFERENCE TO RELATED APPLICATIONS

This application is a continuation of International Application No. PCT/EP2013/073621, filed on Nov. 12, 2013, which claims priority under 35 U.S.C. §119 to Application No. DE 102012022359.5 filed on Nov. 15, 2012, the entire contents of which are hereby incorporated by reference.

FIELD OF THE INVENTION

The invention relates to an attachment for a syringe, a carpule, or the like.

BACKGROUND

Attachments for syringes, carpules, or the like are generally known. They are also used as adapters and serve to provide an attachment means for a cannula or another device, for example an injection device or the like. For example, such attachments that are applied on an extension of the syringe, carpule, or the like are generally provided with an internal thread into which an insert of the cannula can be screwed. Attachments of the type discussed here are frequently configured as security- or tamper-evident-closures and include a first attachment part that is fixedly applied on a terminal extension of a syringe, a carpule, or the like and held there in a locking manner. In closures of this type, a cap is connected to the attachment body via a predetermined breaking line, which cap securely closes the free end of the extension and thus the interior of the syringe, carpule, or the like. If the cap is removed, the predetermined breaking line tears open so that it is irreversibly recognizable that the cap has been removed. Thus a protection against manipulation on the closure is also ensured. The extension includes a free end as well as, at a distance thereto, at least one depression introduced into the outer surface of the extension. An annular groove is preferably provided here wherein the attachment applied on the extension engages in a locking manner. After the placement of the attachment, a syringe, a carpule, or the like is often subjected to a sterilization process wherein, for example, hot steam is used. The high temperatures used during sterilization affect the material of the attachment, which engages under preload on the extension. It is thus possible that the material of the attachment will be compromised or even embrittled such that a secure hold of the attachment on the extension can no longer be ensured. It is also a disadvantage that attachments of the type discussed here, even if they are not subjected to a sterilization process under the effect of heat, are not always held securely enough on the extension, so that during transport or in the handling of the syringe, carpule, or the like. The attachment is inadvertently released. This is particularly undesirable if the attachment is configured as a tamper-evident closure and should close the interior of the syringe, carpule, or the like in a sterile manner. It has also been shown that a rotation of the attachment on the extension is often undesirable.

SUMMARY

An object of the invention is therefore to provide an extension for a syringe, carpule, or the like which does not have the above-mentioned disadvantages.

Accordingly, an attachment is provided for a syringe, a carpule, or the like that includes a distal end, i.e. an end that faces the patient during use. A terminal extension is provided thereon, which has an outer surface, a free end, and at least one depression introduced into the outer surface at spacing to this end.

The extension discussed here is usable not only for a syringe or a carpule, but also, for example, for a pen, adapters for tubing, injection devices, or the like. It is essential that the attachment discussed here interacts with an extension of the above-discussed type and is designed such that a secure connection between the attachment and the extension is ensured. In the following example, it is assumed that the extension is an extension on a syringe or carpule although, as set forth, the extension can also be provided on other, in particular medical devices.

The attachment includes an annular body and can thus be applied to the extension, wherein the base body encloses a free space into which the extension is introducible. The base body comprises two materials, of which a first material is dimensionally stable, and a second material is softer than the dimensionally stable material and deformable. The first material serves to make the attachment easily handleable. By "dimensionally stable material" it is thus meant that even when a certain force is exerted on the extension of a syringe, a carpule, or the like, the attachment can be applied without being permanently deformed or even destroyed. Also when the syringe or carpule is used, during transport, and when handling the attachment before and during use of the syringe or carpule, the attachment must be stable enough that it retains its shape and is thus securely held in place on the extension. The second material is softer and deformable, so that upon applying the attachment to the extension, the second material assumes an inner contour that corresponds to the outer contour of the extension. The base body should find a secure hold on the extension and thus has an engagement region, which engages into at least one depression in the state in which it is applied to the extension. The extension is thus characterized in that its base body includes, along an imaginary circumferential line, at least one first region having the first material and at least one region having the second material. The second material deforms into the at least one depression in the state in which it is applied to the extension, in other words is pressed into the latter, and the second material is embedded into the first material. In the applied state, the imaginary circumferential line is located in the region of the at least one depression of the extension, so that due to the interaction of the two regions that comprise the first and second material, a particularly secure hold on the extension of the syringe or carpule is ensured. The molding of the second, deformable material into the at least one depression is optimally ensured because the second, softer material is accommodated in the dimensionally stable material. This means that the deformable material cannot escape and finds a secure hold in the at least one depression in the outer surface of the extension. This means that the extension is held very securely, and securely held not only when there are axially acting forces that act in the longitudinal direction of the syringe or carpule, or in the direction of a longitudinal axis of the attachment. Moreover, the deformable material being molded into the at least one recess ensures that the attachment is held on the extension such that it cannot rotate with respect thereto, and that with an externally acting torque during a use of the attachment, it does not perform a relative rotation with respect to the extension.

A particularly preferable example embodiment of the extension is characterized in that it is manufacturable with a two-component injection molding method. The above-mentioned first material and also the second material can be used in this injection molding method. This manufacturing method makes it possible to embed the second material into the first material in a simple and cost-effective manner. Moreover, it is possible to realize desired contours, including undercuts, in a simple and inexpensive manner. The relatively free shape design in the manufacture of the attachment makes possible the realization of a high reliability.

Particularly preferable is an attachment that has an annular body on the end of its base body that preferably comprises, viewed in the circumferential direction, segments disposed in the same spacing to one another, which form first regions and are thus comprised of the first material. In the intermediate spaces between these segments, openings, also referred to as pockets, are provided that receive the second material and form second regions. At least one segment includes at least one preferably annularly formed cavity that can be empty but preferably contains the second material. The cavity is delineated by a circular arc-shaped wall section of the segment opposite the cavity. Two wall regions starting from the wall section laterally delimit the cavity, wherein the wall section and the wall region are formed as resilient. The following thus results: if the attachment is plugged onto an extension, radially outwardly oriented forces act, i.e. outward from the cavity, on the wall section, which they press radially outward. The wall regions are thereby deformed such that they are pushed laterally outward; this being the case in particular when the cavity is filled with the second material and prevents an inward displacement of the wall regions. Due to the outward movement of the lateral wall regions, the openings lateral to, i.e., circumferentially delimiting a segment, become narrower. The second material present in these openings is thereby pressed out from the openings and thus molds particularly well into the at least one depression of the extension. This design thus ensures a particularly secure hold of the attachment on a syringe, carpule or the like. The attachment is held securely in a fixed position against axial forces but also against forces acting in the circumferential direction.

According to another example embodiment, a syringe, a carpule, or the like is provided that does not have the above-mentioned disadvantages.

BRIEF DESCRIPTION OF THE DRAWINGS

Example embodiments will now be described with reference to the drawings.

DETAILED DESCRIPTION

Figure 1:
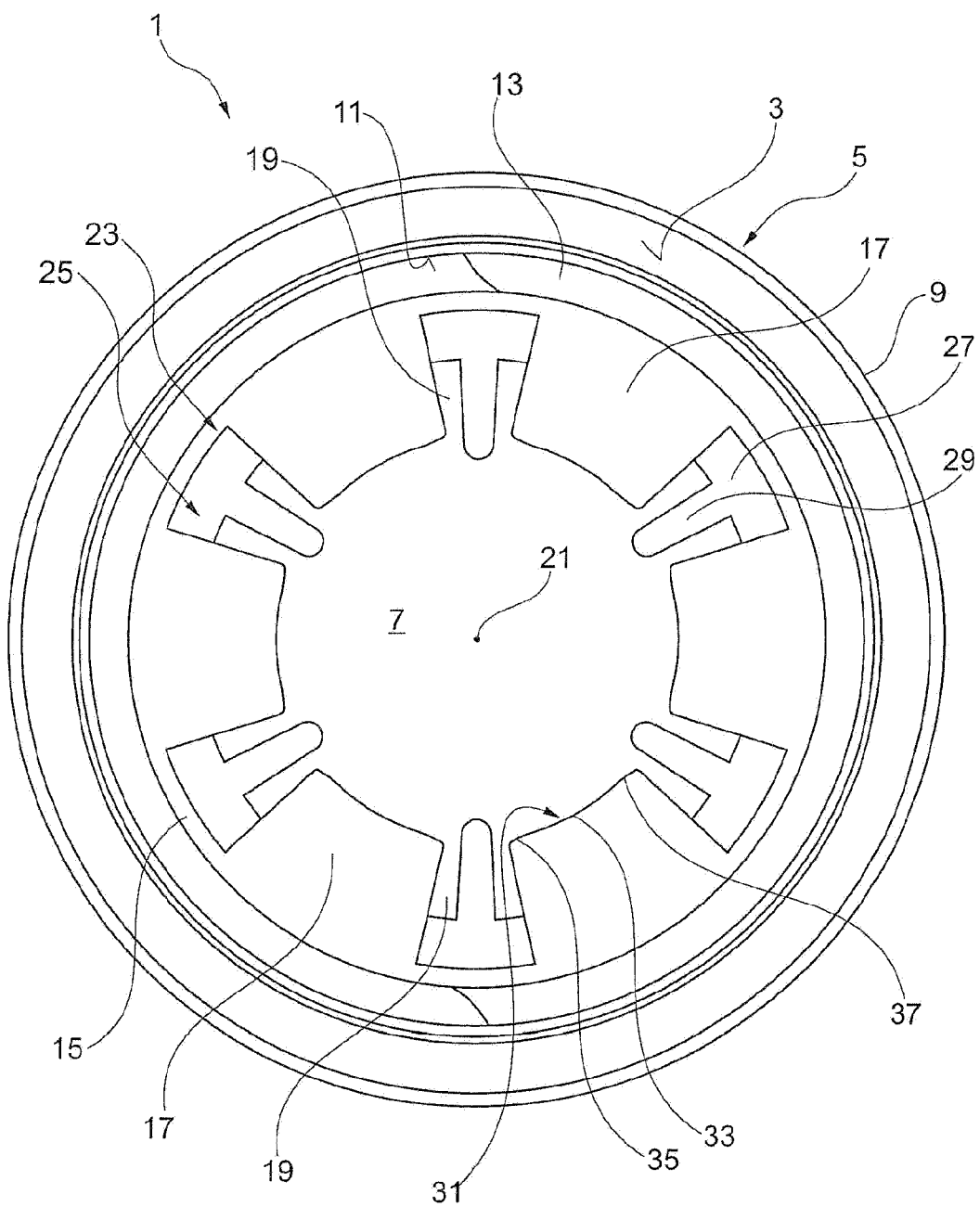
FIG. 1 is a plan view of an end side of a first exemplary embodiment of an attachment according to an example embodiment.

FIG. 1 shows, in plan view, an attachment 1 on its end side 3 according to a first example embodiment. The attachment 1 depicted here is configured such that it can be applied on a syringe, carpule, or the like (not shown), namely on a terminal extension on a distal end of the syringe, carpule, or the like. If the extension is provided on a syringe or carpule, this has a body also referred to as a syringe- or carpule-cylinder having an interior for receiving a substance. The interior can receive one or more substances that are to be administered to a patient, or also serve to receive fluids, in particular from patients, which are to be subjected to a medical examination or treatment. The body includes a distal end on which the extension is provided. It should be noted here again that an extension of this type can also be provided for pens, adapters for tubing, or medical devices, and that here, it is simply assumed as an example that these are extensions on an end of syringes or carpules.

The attachment 1 includes a base body 5, which encloses a free space 7. The base body 5 is preferably formed as cylindrical. The free space 7 is substantially formed as circular so that it can receive the extension of a syringe, carpule, or the like. The base body 5 includes a sleeve section 9, which embraces the extension and is preferably provided with a thread 13 on its inner surface 11. An annular body 15 connects to the sleeve section 9 at a distance to the end side 3, namely on the opposite end of the base body 5; the annular body 15 embraces the extension in an annular region of this extension in a state wherein it is placed on or applied on the extension. The annular body 15 includes at least one segment 17 and at least one opening 19 referred to as a pocket. The at least one segment includes a first material and the at least one opening includes a second material, wherein the first material is dimensionally stable and the second material is softer than the dimensionally stable material, in addition to being deformable.

The example embodiment of the attachment 1 depicted in FIG. 1 is distinguished from a basic version of the attachment including at least one segment and at least one opening in that-seen in the circumferential direction-segments are provided, which are preferably disposed in equal spacing to one another, here six segments disposed in equal spacing to one another. Between the segments 17, which are preferably identically configured, there is at least one opening 19. In a preferred example embodiment, six identical openings 19 disposed in equal circumferential spacing to one another are provided between the segments 17.

The segments 17 and the openings 19 are preferably formed as wedge-shaped and namely such that-viewed towards the center 21 of the free space 7-they taper. The central axis (not shown here) of the attachment 1 extends through this center 21 perpendicular to the image plane of FIG. 1.

The attachment 1 includes a retaining device 23, which includes at least one retaining element 25. In the example embodiment of the attachment including one segment and one opening, only one retaining element is provided. In the example embodiment depicted in FIG. 1 including six segments 17 and six openings 19, the retaining device 23 comprises six retaining elements 25, which are each accommodated in an opening 19, preferably embedded therein. The retaining device 23 serves to securely hold the attachment 1 placed on an extension so that it engages even with the effect of forces in the axial direction or in the radial direction, and that even with forces in the circumferential direction, i.e. torques, it is not released from the extension, but is held securely.

According to an example embodiment of the attachment 1, the retaining elements 25 comprise a base element 27 and an extension 29 extending therefrom. The extension 29 extends centrally from the circular-arcuately configured base element 27. Since the retaining element 25 is accommodated in an opening 19 tapering towards the center 21, and the base element 27 extends over the entire width-measured in the circumferential direction-of the opening 19, the retaining element 25 cannot reach inward into the free space 7. The retaining element 25 is preferably pressed into the opening 19.

The at least one segment 17 has an inner side 31 facing the center 21, i.e. here extending perpendicular to the image plane of the Figure. The spacing of two diametrically opposite inner sides 31 defines an inner radius of the free space 7 that is preferably less than or equal to the outer diameter of an annular region of the extension, not depicted here, of the syringe, carpule, or the like, which in the applied state of the attachment 1 interacts with its annular body 15. The inner diameter of the free space 7 is therefore preferably also smaller than the outer diameter of the annular region of the extension such that upon application on the extension the attachment 1 is widened and for this reason is already held on the outer surface of the extension by frictional forces.

The inner side 31 can be configured as a flat surface with respect to whose centerline a radial line emanating from the center 21 is perpendicular.

Preferably the central region 33 is configured as circular arc-shaped and is disposed on an imaginary circle whose center point falls in the center 21. Outer lateral regions 35 and 37 preferably connect—as seen in the circumferential direction—to the central region 33, which lateral regions 35 and 37 fall off outwards starting from the central region 33, i.e. have an increasing distance to the center 21.

The ends of the extensions 29 of the retaining elements 25, which ends face the center 21, lie at a measured distance to each other—along an imaginary diameter line—which is smaller than the distance between the segments 17 opposite the central regions 33.

The attachment 1 according to the first example embodiment thus includes at least one segment 17 and at least one opening 19, each including a retaining element 25 and a retaining device 23, preferably, as depicted in FIG. 1, six segments 17 distributed in the circumferential direction, six openings 19 disposed between the segments 17 with six retaining elements 25. If an attachment 1 of the type described here is plugged onto a syringe, carpule, or the like, then the annular body 15 lies in the region of the annular surface of the attachment. The annular body includes—seen in the circumferential direction—at least one first region, which is formed by the inner side 31 of a segment 17, and at least one second region, which is defined by the retaining element 25, here by its extension 29. A plurality of segments 17 and a plurality of openings 19 are particularly preferably provided, which alternate in the circumferential direction.

The attachment 1 includes in its at least one first region a first dimensionally stable material, and in its at least one second region a second material, which is softer than the first material and deformable. If an attachment of this type is thus applied to an extension, then the second, soft material of the at least one, preferably of the six second regions, is molded or pressed into a depression in the outer surface of the extension. It is provided here that the number of depressions in the outer surface of the extension is preferably matched to the number of the second regions wherein the softer, deformable material is provided.

In the attachment 1 shown in FIG. 1, which includes six second regions including the retaining elements 25 and their extensions 29, six depressions disposed in the same circumferential spacing to one another are thus preferably provided in the annular region of the extension. However, this also means that an attachment 1, which is plugged onto an attachment of this type, should be disposed in a rotational position wherein the second regions including the softer, deformable material directly oppose an associated depression. However, the application of an attachment 1 on an extension is simplified in that in particular it is provided that in the annular region of the extension an annular groove is provided as at least one depression, the base of which annular groove has a smaller outer diameter than the region of the outer surface directly connecting as viewed towards the free end of the extension. In this way a shoulder is formed between the outer surface and the base of the annular groove, on which shoulder the attachment 1 abuts after being placed on the extension. An axial pulling-off of the attachment from the extension is thus prevented with a very high degree of certainty.

In addition, since the soft material of the second region of the attachment 1 is pressed flat into the depression formed as an annular groove and thus directly abuts on the extension, it is also prevented with a high degree of certainty by the frictional forces generated by the pressing and molding of the soft material that the attachment 1 twists undesirably with respect to the syringe or carpule with generation of a torque.

Figure 2:
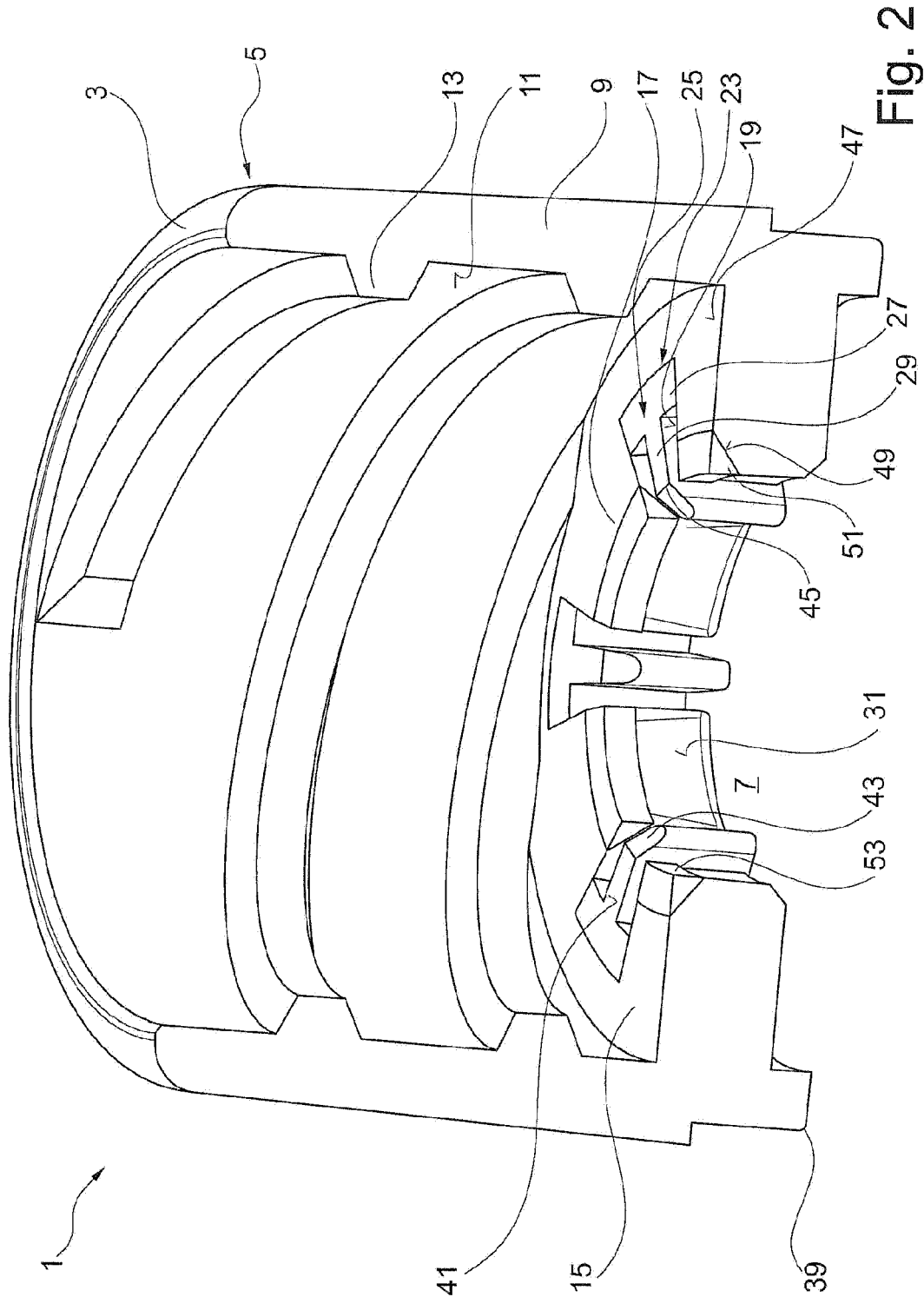
FIG. 2 is a perspective view of an attachment cut away in a longitudinal direction according to a second example embodiment.

FIG. 2 shows an attachment 1 in perspective view, in which the attachment 1 is cut away in the longitudinal direction according to a second example embodiment.

The example embodiment reproduced in FIG. 2 of the attachment substantially corresponds to that depicted in FIG. 1. Identical and functionally identical parts are provided with identical reference numbers. In this respect reference is made to the description for FIG. 1.

First the similarities of the second exemplary embodiment reproduced in FIG. 2 that arise with respect to the first exemplary embodiment according to FIG. 1 will be discussed:

The attachment 1 includes an end side 3 which has been reproduced in plan view in FIG. 1. The base body 5 of the attachment 1 includes a sleeve section 9, which is generally cylindrically formed and is provided with a thread 13 on its inner surface 11. On the end 39 of the base body opposite the end side 3 the annular body 15 is provided, which includes at least one segment 17 and at least one opening 19, as is the case with the basic shape of the attachment 1 explained based on FIG. 1. However, it is preferably also provided in the example embodiment according to FIG. 2, as in the attachment 1 according to FIG. 1, that the annular body 15 includes six segments 17 disposed in the same spacing to one another as viewed in the circumferential direction and six openings 19 lying therebetween. Here a retaining device 23 is also provided, which comprises a retaining element 25 in the basic shape of the attachment 1, here in the exemplary embodiment according to FIG. 2, six retaining elements 25 of this type, which are each disposed in an opening 19.

FIG. 2 shows that the retaining element 25 also includes, besides the base element 27, the extension 29 which emanates centrally, as in the exemplary embodiment according to FIG. 1, from the base element 27 and extends in the radial direction, i.e. towards the center 21, not reproduced in FIG. 2, of the free space 7.

In the example embodiment according to FIG. 2 the segments 17 also form first regions made from a first material, and the retaining elements 25 form second regions made from a second material, wherein the material properties are identical, as explained with reference to FIG. 1.

The example embodiment of the attachment 1 according to FIG. 2 differs in the following aspects from the example embodiment according to FIG. 1:

The surface 41 of the extensions 29 oriented towards the end side 3 includes in its end region facing the free space 7 an inclined surface 43 which declines starting from the surface 41 over a bend 45 downwards towards the end 39 of the attachment 1.

It should be indicated here that an inclined surface of this type can also be provided very well in the example embodiment according to FIG. 1.

The example embodiment of the attachment 1 according to FIG. 2 also differs in that the upper side 47 facing the end side 3 of the at least one segment 17, here all segments 17, has a slope 49 in a region facing the free space 7, which slope 49 falls away from the upper side 47 in a direction that is oriented away from the end side 3. A wedge 51, which is part of the retaining device 23, is placed on the slope 49. It is comprised of the second material, which is softer than the dimensionally stable first material and also deformable. A wedge 51 of this type is provided on at least one of the segments 17, but preferably on all of them, so that six wedges 51 configured as ring-segment shaped are present at the ends of all of the segments 17.

The upper side of the wedge 51 facing the end side 3 constitutes an extension of the upper side 47 of the segments 17.

It is preferably provided that one of the front sides 53 of the wedge 51 facing the free space 7 projects towards the center 21 over the respective inner side 31 of an associated segment 17.

This example embodiment is preferably provided in all six segments 17, but is not mandatory.

According to the first and second example embodiments shown in FIG. 1 and FIG. 2, preferably all segments 17, openings 19, and all elements of the retaining device 23 are configured identically, i.e., the retaining elements 25, the base elements 27, the extension 29, and the wedge 51, which, however, is only provided in the exemplary embodiment according to FIG. 2.

The wedges 51 yield a larger abutment surface for the softer material at the extension compared to the exemplary embodiment according to FIG. 1. The inclined surfaces 43 configured as wedge surfaces push the softer material of the wedges 51 more strongly against the extension and compress it into the at least one depression if there is an attempt to pull the attachment 1 off the extension. An improved hold of the attachment thus results with axially acting tensile forces.

Figure 3:
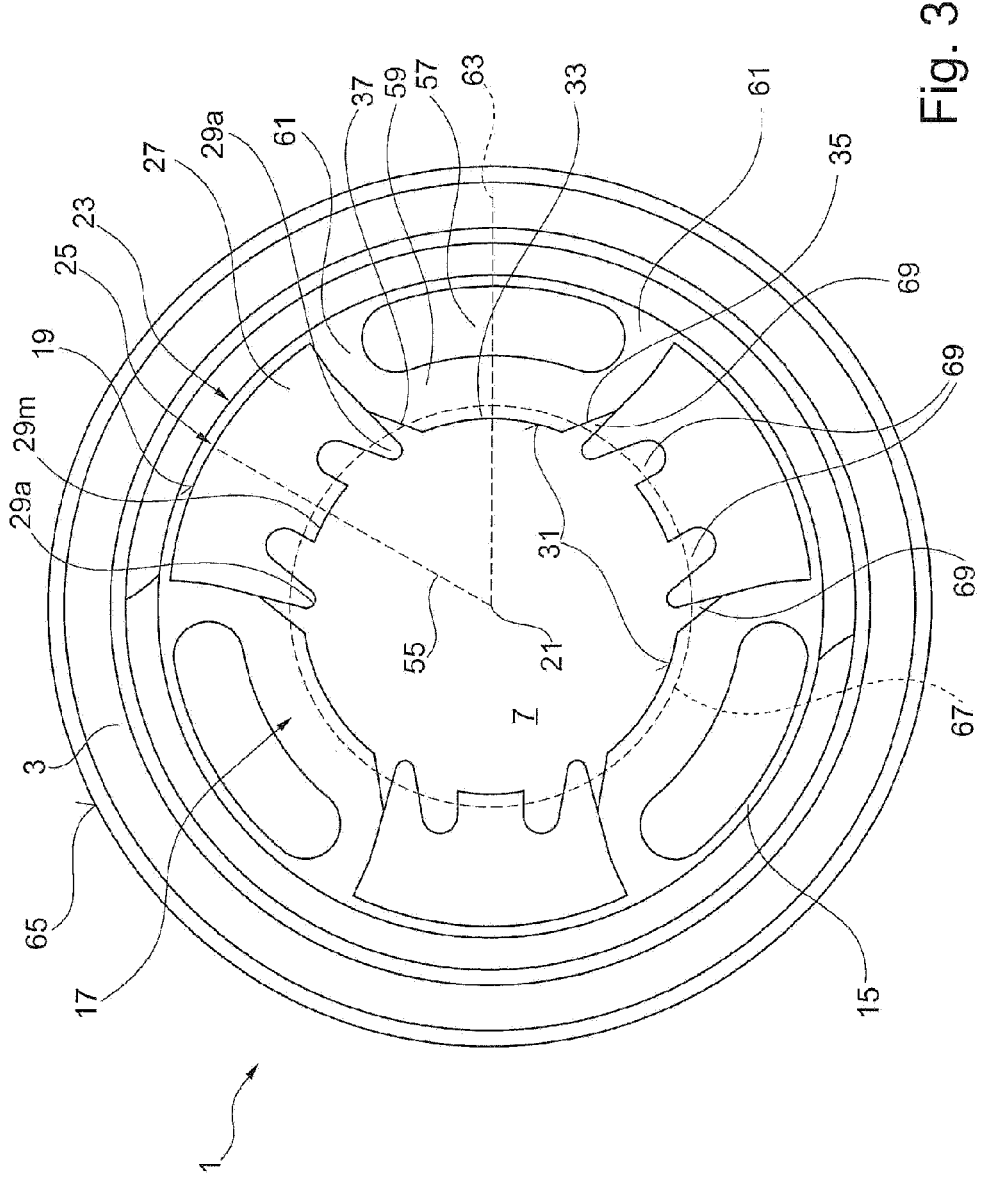
FIG. 3 is a plan view of an end side of an attachment according to a third example embodiment.

FIG. 3 shows a further example embodiment in plan view of an attachment 1. In FIG. 3, as in FIG. 1, the viewer is also facing the end side 3 of the attachment 1. Identical and functionally identical parts are provided with identical reference numbers as have also been used for the preceding figures. In this respect reference is made to the description of FIGS. 1 and 2.

The example embodiment of the attachment 1 according to FIG. 3 can be configured such that it includes only one segment 17 and only one recess 19. However, it is preferably also provided that the example embodiment of the attachment 1 shown in FIG. 3 includes three segments 17 disposed in identical circumferential spacing to one another and three openings 19, also referred to as pockets, lying therebetween. This attachment 1 also includes a retaining device 23, which in the basic shape of the attachment 1 comprises a retaining element 25 provided in the one opening 19 of the attachment 1. Correspondingly there are three retaining elements 25 here that are respectively accommodated in the three openings 19.

Preferably all of the retaining elements 25 are identically configured. Each retaining element comprises a base element 27 which abuts on the base of the opening 19 facing away from the center 21 and is preferably configured in a circular arcurate manner. In contrast to the exemplary embodiment of the attachment 1 according to FIGS. 1 and 2 it is provided here that two extensions 29a of the base element 27, disposed symmetrically to a central axis 55 of the retaining element 25 are provided, which, like the extensions of the example embodiments according to FIGS. 1 and 2, include an end protruding into the free space 7, which in particular is rounded, as is also the case in the exemplary embodiments according to FIGS. 1 and 2.

In addition, as shown in FIG. 3, the base element 27 includes a central projection 29m whose end side is formed as symmetric to the center axis 55 intersecting the center 21 and is preferably arcurately curved; it could also be formed as flat as described above.

Not only the retaining elements 25, but also the segments 17 of the attachment 1 according to FIG. 3 are all identically constructed. Here it is provided that the segments 17 include at least one cavity 57 preferably configured as having a ring-segment-shape, which is filled with air, or preferably with the second material explained with reference to FIGS. 1 and 2. A segment can also include a plurality of preferably adjacent cavities.

The cavity 57 is delineated with respect to the free space 7 by a circular arc-shaped wall section 59. In addition-viewed from the circumferential direction-the wall regions 61 projecting from the ends of the wall section 59, which are preferably formed with mirror-symmetry to a central axis 63 of the segment 17 that intersects the center 21.

The inner side 31 of each segment 17 is preferably formed as circular arc-shaped in a central region 33, and is outwardly inclined in leftwardly and rightwardly connecting lateral regions 35, with mirror-symmetry to the central axis 63, i.e., the lateral regions 35 and 37 fall away with respect to the central region 33, i.e. towards the outer circumferential surface 65 of the attachment 1.

In the example embodiment according to FIG. 3 it is also provided that the at least one segment 17 or the three segments 17 are part of an annular body 15, wherein the segments 17 and the openings 19 with the retaining elements 25 realize, along an imaginary circumferential line, at least one first region, formed by the segments 17 with a first material, and at least one second region, formed by the retaining element 25, with a second material.

In FIG. 3 a dashed line 67 is drawn, which shows the course of the outer surface of an extension of a syringe, carpule, or the like, and namely in the region of the at least one depression of the extension, which is preferably configured as an annular groove. Here the line 67 represents the base of this groove.

It can be seen that the diametrically measured distance of an inner side 31 of a segment 17 to an inner surface of the extension 29m facing the center 21 is smaller than the inner diameter of the line 67. Accordingly, in the example embodiment of the attachment 1, the outer surface of the extension also extends in accordance with FIG. 1.

It can be seen that when the attachment 1 is inserted into an extension, the inner sides 31 of the segments 17 and the ends of the extension 29 or the extensions 29*a* and 29 *m* facing the center 21 are pushed radially outward. This results in the following:

With a force acting from the center 21 radially outward on the wall section 59, the lateral wall regions 61 of the segments 17 are deformed, namely from the central axis 63 outward towards the laterally adjacent openings 19. This outward movement of the wall regions 61 is particularly pronounced if the cavity 57 is filled with the second deformable material of which the retaining elements 25 are also comprised.

The free space of the openings 19 is thus laterally narrowed by the outwardly forced wall regions 61 such that the retaining elements 25 accommodated in the openings 19 are compressed. The second material, which the retaining elements 25 contain, or of which the retaining elements 25 are preferably comprised, is thereby forced inward towards the center 21 and molded into the at least one depression in the outer surface of the extension. In order to avoid the necessity of assigning a depression, distributed in the circumferential direction, to each retaining element 25, which limits a correct positional alignment of the attachment 1 with respect to the extension, the at least one depression is preferably configured as an encircling groove in the outer surface of the extension, as has already been noted above.

With the insertion of the attachment 1 into an extension, radially outward forces, i.e. forces directed away from the center 21, are exerted on the retaining element 25, so that its at least one projection, i.e., here the projections 29*a* and the projection 29*m*, are forced outward. This means that free spaces 69 laterally adjacent to the extensions 29*a* and recesses 69 provided in the inner side of the retaining elements 25 facing the center 21 are filled with the second material of the holding elements 25, which material is pushed from inside to outside and outside to inside, wherein the forced material of the retaining elements 25 is also molded into or pressed into the at least one depression or annular groove in the outer surface of the extension.

In the two regions of the attachment 1 realized by the retaining elements 25, a deformable second material is thus pushed against the outer surface of the extension, namely in the region of the preferably annular depression. This relatively soft material generates relatively high frictional forces with the extension so that on the one hand very good protection against an axial pulling-off of the attachment 1 is ensured, but a relative rotation of this attachment 1 with respect to the extension is also prevented. This is particularly the case because in the design of an annular groove in the outer surface of the extension, a shoulder projecting towards the outer surface is formed that securely prevents a pulling-off of the attachment towards the free end of the extension.

Furthermore, it can be seen that the lateral regions 35 and 37 of the segments 17 each form a wedge surface, due to which, with the introduction of a torque in the attachment 1, the second material is forced against the outer surface of the extension or into the at least one depression and compressed into it. The frictional forces between attachment 1 and the extension of a syringe or carpule are thus further reinforced by the inclined lateral regions 35 and 37.

The same particularly preferred effect occurs in particular in the example embodiment shown in FIG. 1, where the inner side 31 of the at least one segment or the segments 17 also include two lateral regions 35 and 37 which extend in a wedge-shaped manner with respect to the central region 33 and into which the material of the extension 29 of the retaining element 25 is forced when an attachment 1 is plugged into an extension. Thus, here too, when a torque is applied to the attachment 1 as shown in FIG. 1, a greater frictional force is generated, which secures the attachment against a relative rotation with respect to the extension.

It was explained above that the segments 17 and the openings 19 taper towards the free space 7 However, this is not mandatory. Other preferred designs can also very well be chosen wherein segments 17 or openings 19 widen towards the free space. FIG. 3 shows an alternative example embodiment in which the openings 19 starting from their outer base surfaces initially taper towards the free space 7 but then widen. The outer surfaces of the base elements 27 lying in the openings 19 are configured accordingly. The outer surfaces of the adjacent segments 17 are configured as complementary thereto.

Figure 4:
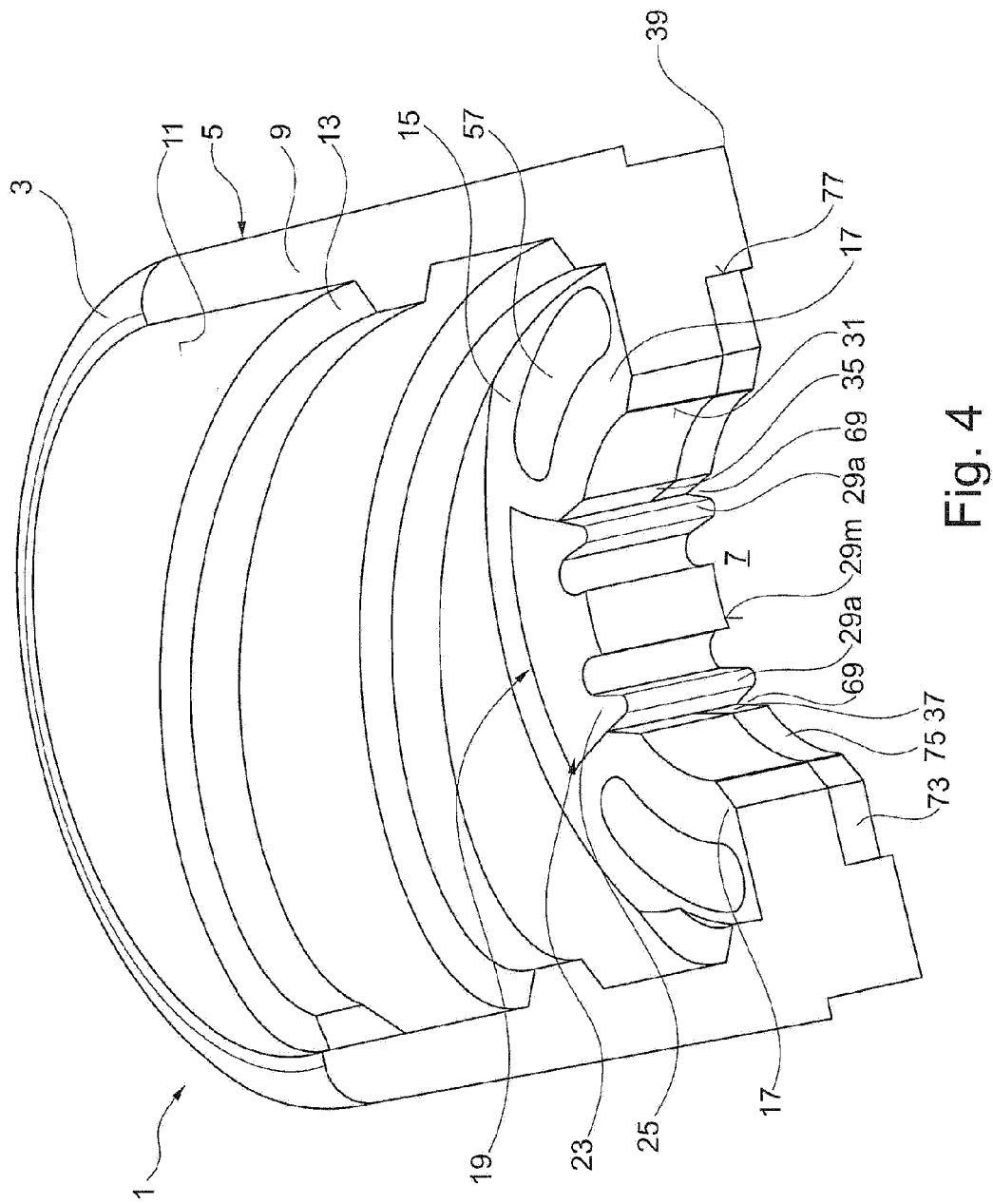
FIG. 4 is a perspective view of a cutaway of the second example embodiment according to FIG. 3.

FIG. 4 shows the attachment 1 according to FIG. 3 in perspective view. The attachment 1 is cut away in the longitudinal direction. Identical and functionally identical parts are provided with identical reference numbers as have also been used for the preceding figures.

FIG. 4 shows that the attachment 1 includes an end side 3 and a base body 5 from whose inner surface 11 a thread 13 extends. This allows the neck of a cannula to be screwed into the attachment 1 which is thereby fixedly connected to a syringe, carpule, or the like. When screwing-on the cannula it should be prevented that the attachment 1 rotates with respect to the extension, and thus a secure attaching of the cannula is ensured.

The sectional view shows that the attachment 1 includes a sleeve section 9 and an annular section 15, which is disposed on the lower end of the base body 5 of the attachment 1. Clearly recognizable here are two segments 17 and an opening 19 lying therebetween, into which the retaining elements 25 of the retaining device 23 are introduced.

The perspective view clearly shows wedge-shaped free spaces 69 which are present to the right and left adjacent to the lateral extensions 29*a* of the retaining element 25 and are delimited by the lateral regions 35 and 37 of the inner side 31 of the segment 17.

FIG. 4 also allows the cavities 57 in the segments 17 to be recognized.

The perspective depiction of this figure also shows that the retaining device 23 can preferably also be supplemented by a layer 73 attached from below to the attachment 1 in the region of the end 39, which layer 73 comprises the deformable second material, or preferably is comprised thereof. Moreover, it can also preferably be provided that the front side 75 of this layer opposite the inner side 31 of the segments 17 projects towards the center 21 not depicted here. The layer 73 is preferably delimited on the side facing away from the center 21 or the free space 7 by a step 77 of the annular body 15, which supports the layer 73 so that upon placing the attachment 1 on an extension the second material of the layer 73 is forced against the at least one depression in the outer surface of the extension, preferably into the annular groove of the extension. In this way the retaining device 23 produces additional frictional forces that secure the attachment 1 against twisting with respect to the extension.

The following applies with reference to the exemplary embodiment according to FIG. 2:

On the one hand it is also possible to provide the wedge 51, depicted in FIG. 2, of the retaining device 23 in the attachment 1 according to FIG., either instead of the layer 73 or in addition thereto.

Accordingly, in the example embodiment shown in FIG. 2, the wedge 51 can be supplemented by a layer 73 or replaced thereby.

Finally in the example embodiment depicted in FIG. 4 it is also possible to provide at least one inclined surface in the retaining element 25, which was indicated in FIG. 2 by the reference number 43.

Figure 5:
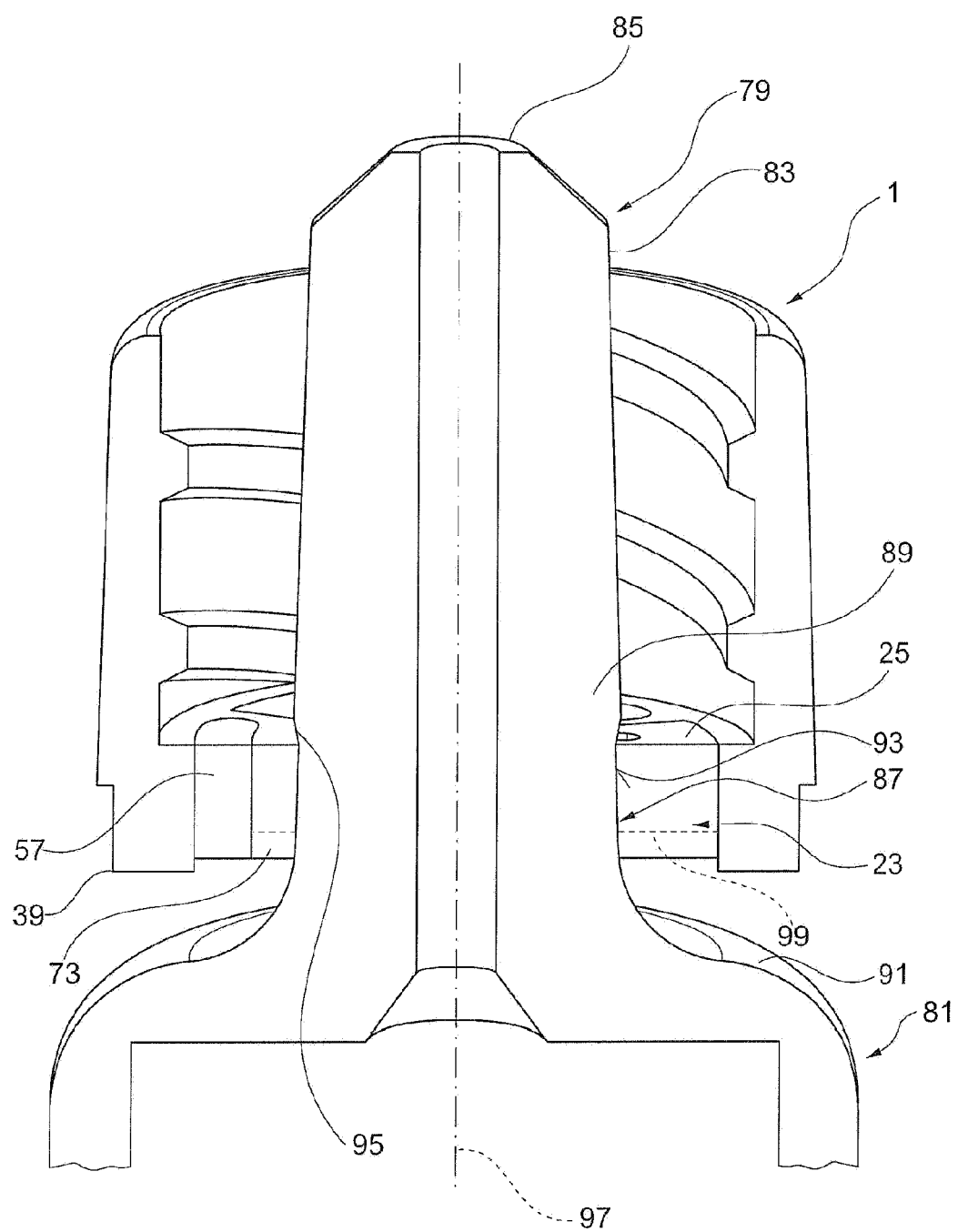
FIG. 5 is a sectional view of the attachment plugged onto an extension of a syringe or carpule according to the third example embodiment.

FIG. 5 shows an attachment 1 in longitudinal section, which is applied to an extension 79 of a syringe, a carpule 81, or the like. Identical conditions apply as when applying an attachment according to the preceding FIGS. 1 to 4; the same conditions result, so that the explanations for the attachment according to FIG. 5 in connection with the extension 79 apply to all exemplary embodiments. Here, as explained above, the extension can also be part of a pen or an adapter that is configured as a connector for a medical device or a tube.

Reference should be made to the explanations for FIGS. 3 and 4 with respect to the details of the attachment 1.

The extension 79 includes an outer surface 83 wherein at least one depression 87 is introduced at a distance from the free end 85. It is preferably provided that this depression is configured as an annular groove whose outer diameter is smaller than the outer diameter of the outer surface in a region 89 of the extension 79, which region 89 lies outside the annular groove. The term "outside" here refers to the depiction according to FIG. 5, wherein the distal end 91 of a syringe or carpule 81 is disposed according to the view in FIG. 5 above, so that the extension 79 extends upward from here.

Since there is a smaller outer diameter in the region of the depression 87, an outwardly projecting shoulder 95 is formed opposite the bottom of the depression, said shoulder preventing an upward pulling-off of the attachment 1 towards the central axis 97 of the extension 79.

It has been explained in connection with FIG. 4 that in the region of the end 69, a layer 73 is provided which is part of the retaining device 23. It is clear from the sectional view chosen here of the attachment 1 that the layer 73, which is defined here by a dashed line 99, can also be an integral part of the retaining element 25 and/or of the cavity 57.

It can be seen from FIG. 5 that after the insertion into an extension 79 the annular region 15 of an attachment 1 is disposed in the region of an annular surface of the extension, which annular surface lies above the distal end 91 of the syringe or carpule. The at least one depression 87 is provided inside this annular surface of the extension 79, preferably the above-mentioned annular groove. After the placing of the attachment 1 onto the extension 97 the first and second regions of the attachment 1 lie in the region of the annular surface of the extension; the first and second regions of the attachment are realized on the one hand by the segments 17, and on the other hand by the retaining elements 25. Here in the region of the annular surface of the extension 79, the second material of the attachment 1, which is deformable, is molded onto the extension 79 so that it abuts directly on the extension and secures it, due to high frictional forces, against axial pulling-off and against a twisting with respect to the extension 79.

Figure 6:
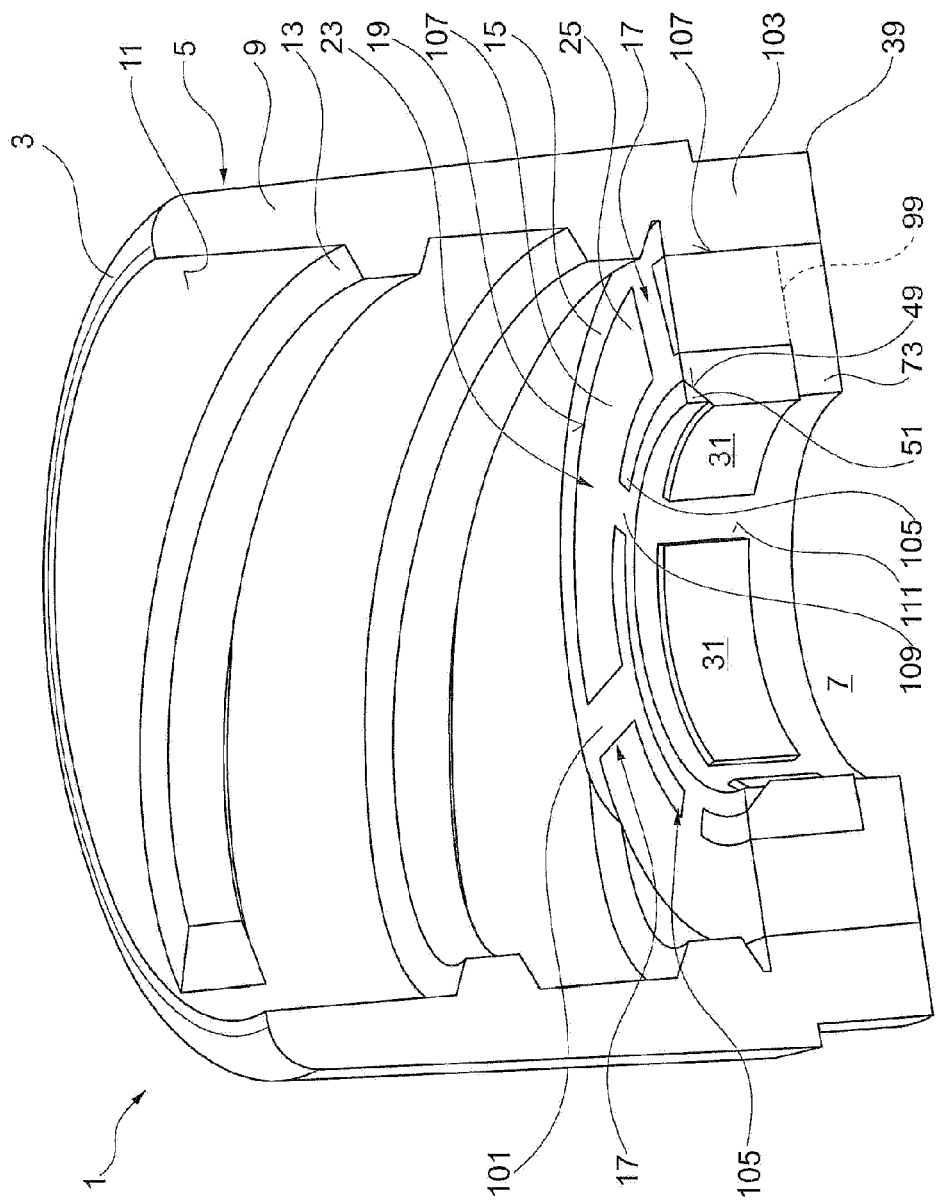
FIG. 6 is a perspective view of an attachment cut away in a longitudinal direction according to a fourth example embodiment.

FIG. 6 shows in perspective view a longitudinal section through a further exemplary embodiment of an attachment 1. Identical and functionally identical parts are provided with identical reference numbers so that reference can be made to the preceding description.

The attachment 1 includes a base body 5 including an end side 3 and a sleeve section 9 including an inner surface 11, on which a thread 13 is provided. The attachment 1 also includes an annular body 15, which comprises at least one segment 17 and at least one opening 19. It is also provided here that the attachment 1 includes segments 17 disposed at identical distances to one another and openings 19 lying therebetween.

The attachment 1 depicted here also includes a retaining device 23 including a retaining element 25 accommodated in an opening 19, wherein preferably a retaining element 25 is associated with each opening 19.

The segments 17 include an inner surface 31, which faces the interior 7 and is directed towards the center 21, not depicted here. Each segment 17 comprises a bridge 101 via which it is connected to an outer wall 103 of the annular segment 15. The bridge 101 extends radially towards the center 21 and includes a wall segment 105 which projects laterally with respect to the bridge 101, preferably symmetrically to the right and left thereof.

The wall segments 105 of two adjacent bridges 17 extend along an imaginary circumferential line but end at a distance to each other so that a cavity 107 is formed which is preferably filled with the above-explained second material, while at least the segment 17, preferably the entire remaining attachment 1, contains the first material, preferably is comprised thereof.

The width of the bridges 101 of the segments 107 is substantially smaller than the width of the wall segments 105 measured in the circumferential direction. For example, the width of the wall segments 105 is two to ten times larger than the width of the bridges 101, preferably five to seven times larger. The bridges 101 and the wall segments 105 are thus T-shaped in the broadest sense.

The cavities 107 include the second material; they are preferably completely filled therewith, wherein the second material extends through intermediate spaces 109 lying between the ends of the wall segments 105 out into the free space 7.

A layer 73 can preferably be provided below the segments 17, which layer contains the second material, preferably is comprised thereof. It is indicated by the dashed line 99 that the layer 73 can be an integral component of the second material in the cavity 107.

Instead of the layer 73, preferably in addition to it, a wedge 51 made from the second material is also provided here, said wedge being provided on a slope 49 of the segments 17. The wedge 51 also includes the second material and is preferably comprised thereof. The wedge 51 and the layer 73 are part of the retaining device 23.

It can be recognized from FIG. 6 that the inner side 31 of the segments 17 preferably projects somewhat with respect to the inner surface 111 of the second material, which inner surface 111 faces the interior 7. This design has the advantage that when the attachment 1 is applied to an extension 79, the first region of the attachment 1 —the first region being formed by the inner surfaces 31 of the segments 17 —enters into engagement with the outer surface of the extension 79 so that the second material, which is softer than the first material in the first region when the attachment 1 is initially applied, does not come into contact with its outer surface and is not ablated by the frictional forces.

The attachment 1 according to FIG. 6 thus includes the mentioned first regions, including the first material, and also second regions, which are formed by the second material.

In the applied state of the attachment 1, radially outward directed forces act from the center 21 outward so that the wall segments 105 are forced outward towards the outer wall 103 of the attachment 1. In this way the second material present in the cavities 107 is compressed and forced out of the intermediate spaces 109 and, in the region of the layer 73, inward into the interior 7. In the applied state, this displacement of the second material causes it to be forced against the at least one depression, thus here against the annular depression 87 in the outer surface 93 of the extension 79 (see FIG. 5) and deformed into the depression, i.e. compressed into it.

High frictional forces thereby result, due to which the attachment 1 is not only secured in the axial direction on the projection 79, wherein the shoulder 95 provides a particularly good axial hold, there is also protection against undesirable twisting of the attachment 1 with respect to the extension 79.

Figure 7:
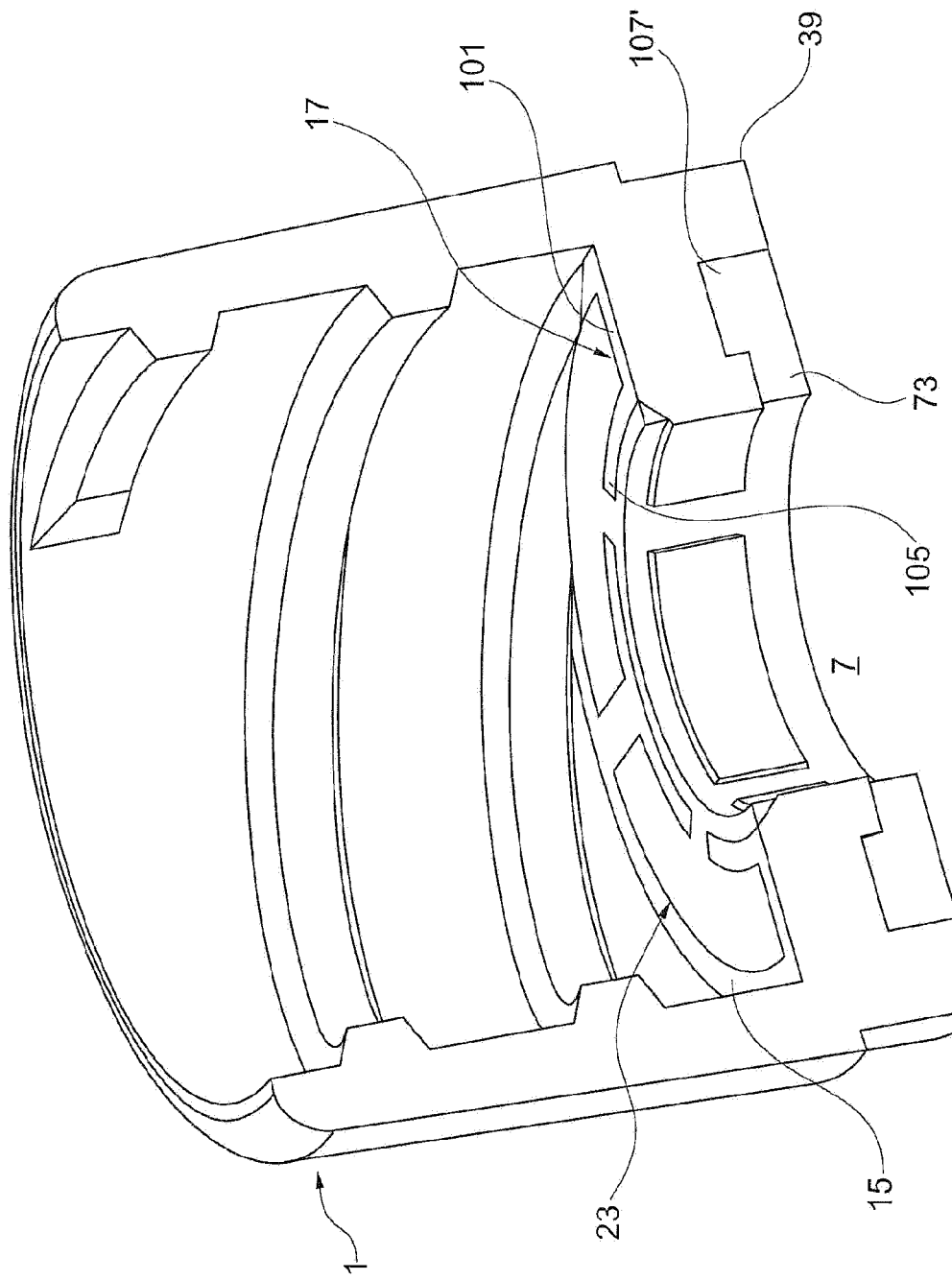
FIG. 7 is a perspective view of the attachment cut away in another plane in the longitudinal direction according to the fourth example embodiment.

Finally FIG. 7 shows the attachment from FIG. 6 in perspective view in longitudinal section, however wherein the sectional plane lies in another plane than is the case in FIG. 6.

Identical and functionally identical parts are designated by like reference numerals, so that reference can be made to the preceding description.

From the sectional plane according to FIG. 7 it can be seen that the bridge 101 of the segments 17 preferably do not extend over the entire height of the annular body 15, but rather at a distance to the edge 39. Here it can preferably be provided that the distance of the bridge 101 to the lower edge is somewhat larger than the distance of the wall segment 105. If upon applying the attachment 1 to an extension 79 the wall segment 105 displaces a cannula or syringe 81 outward in the radial direction, then a cavity 107' is also formed here in the region of the layer 73 of the retaining device 23, into which the material of the layer 73 is compressed and thus forced forward towards the free space 7. This improves the abutment of the second material, which the retaining device 23 contains, or of which the retaining device 23 is comprised. This design thus improves the molding of the second material of the layer 23 onto the at least one depression or onto the preferably provided annular groove 87 of the projection 79.

The following is clear from the explanations of the figures:

In its various example embodiments, the attachment 1 includes a base body, which contains two materials, preferably is comprised thereof. A first material is dimensionally stable and a second is softer than this material, also deformable. The base body 5 of the attachment 1 has an annular region 15 with a first region and a second region. The first region is formed by segments and the second region by retaining elements 25 of a retaining device. The segments are comprised of the first material and the retaining elements 25 of the second material. The annular region 15 thus forms an engagement region, which in the placed-on state of the attachment 1 on an extension 79 engages a syringe, a carpule, or the like into at least one depression 87 in the outer surface 83 of the extension 79. The attachment is characterized in that the second material is molded or pressed into the at least one depression, or in other words, compressed into it. In this way high frictional forces are generated that hold the attachment securely on the extension.

The attachment 1 is particularly preferably manufactured using a two-component injection molding method whereby the first and second materials are used in this case. The figures show that the first and second regions have different contours and that the retaining device 23 comprises various partial elements, namely the retaining element 25, the wedge 51, and/or the layer 73. The base body 5 of the attachment 1 preferably includes the first material, in particular is comprised thereof. Correspondingly the retaining element 25 includes the second material and is preferably comprised thereof. It is also possible to make the various contours of the attachment 1, as can be seen from FIGS. 1 to 7, with a simple two-component injection molding method, wherein the two materials are molded into each other. The realization of the attachment 1 is thus relatively economical.

The first material preferably includes temperature-resistant, in particular high-temperature-resistant plastics, preferably polycarbonates, polysulfones, or polypropylenes, or is comprised only of these plastics. The second material is preferably comprised of soft plastics, in particular thermoplastic elastomers such as TPE (thermoplastic elastomer), PTFE (polytetrafluoroethylene), soft PVC (polyvinyl chloride) or silicone. In particular the second material is completely comprised of these substances. Hard and soft copolymers can also be used respectively for the first and second material.

A syringe or carpule 81, which is to be closed by an attachment 1 of the type discussed here, includes an interior for receiving a substance which either is to be administered to a patient or is obtained, in particular from the patient, in order to subject it to an evaluation or treatment, optionally in order to administer it to the patient again.

The body referred to as the syringe cylinder or carpule cylinder includes a distal end 91 from which a terminal extension 79 emanates, which has an outer surface 83. At least one depression 87 is introduced therein, and namely at such a distance from the free end 85 of the extension 79 that upon applying an attachment 1 it is disposed in the region of an annular surface in which the annular body 15 of the attachment 1 comes to rest. The extension 79 preferably includes a continuous annular groove as depression 87, which is delimited in the direction of its free end 85 by a shoulder 95 so that an axial pulling-off towards the central axis 97 of the extension 79 is made very difficult.

The second material of the attachment 1 is deformable such that after application, it is forced into the at least one depression and molded into the depression. The deformable second material is preferably chosen such that high frictional forces arise between the outer surface of the extension 79. In this way an undesirable twisting of the attachment 1 with respect to the extension 79 is also prevented.

Free spaces 69 are preferably provided, which are formed in particular by inclined lateral regions 35 and 37 of the segments 17. Here the second material is pressed particularly well against the outer surface of the extension 79, whereby it is ensured due to the wedge shape that particularly high forces act against an inadvertent twisting of the attachment 1 with respect to the extension 79.

The attachment 1 is preferably configured and dimensioned such that it can be used on conventional extensions 79 of all types, which include, in particular, a conical outer surface 83 that tapers towards the free end 85 of the extension 79. It is thus possible to use the advantages resulting from the attachment 1 even with conventional syringes and/or carpules.

In summary, an attachment for a syringe, a carpule 81 or the like, is provided which has a distal end 91 and thereon a terminal extension 79, wherein the extension 79 includes an outer surface 83, a free end 85, and at least one depression 87 introduced into the outer surface at a distance to the free end 85, wherein the attachment 1 has an annular base body 5 and is placeable onto the extension 79, wherein the base body 5 encloses a free space 7, into which the extension 79 can be introduced, wherein the base body 5 comprises two materials, is preferably composed of them, of which a first material is dimensionally stable and a second material is softer than the dimensionally stable first material and is deformable, and wherein the base body 5 includes at least one engagement region, which in a state in which the base body is plugged into the extension 79 engages into the at least one depression 87, characterized in that along an imaginary circumferential line, the base body 5 has at least one first region including the first material, and at least one second region including the second material, wherein in a state in which it is plugged onto the extension 79 the second material is molded into the at least one depression 87, and wherein the second material is embedded into the first material.

According to an example embodiment, the attachment is characterized in that with use of the first material and the second material the base body 5 is manufacturable using a two-component injection molding method. The Attachment is further characterized in that the base body 5 includes the first material, and in a circumferential region comprises at least one opening 19 in which the second material is provided, which forms the second region.

According to another example embodiment, the attachment is characterized in that on one end 39 the base body 5 includes an annular body 15, which in a state in which it is applied to the extension 79 embraces an annular region of the extension 79, wherein the at least one depression 87 is disposed in this region of the extension 79. The at least one depression 87 is of annular design.

According to a further example embodiment, the attachment is characterized in that the annular body 15 includes in a circumferential direction segments 17 which are, preferably disposed at the same distance to one another, and which form the first regions, and openings 19 in the intermediate spaces between the segments, which receive the second material and which form second regions. The segments 17 and the openings 19 taper towards the free space 7.

According to yet another example embodiment, the at least one segment 17 includes at least one, preferably annularly formed cavity 57, which preferably contains the second material, wherein the at least one segment 17 comprises a circular arc-shaped wall section 59, which delimits the at least one cavity 57 with respect to the free space 7, and wall regions 61 emanating from the ends of the wall section 59, which wall regions 61 laterally delimit the at least one cavity 57, wherein the wall section 59 and the wall regions 61 are formed as being resilient so that with a force acting from the free space 7 on the wall section 59 the wall regions 61 are forced laterally outward, and thus the widths measured in the circumferential direction of the laterally adjacent openings 19 are reduced.

According to an example embodiment, the at least one segment 17 includes an inner surface 31 facing the free space 7, which preferably comprises two lateral regions 35, 37 adjacent to a central region 33. The at least one segment 17 includes an upper side 47, and that in a region of the upper side 47 facing the free space 7, a slope 49 is provided on which a wedge 51 is placed.

According to another example embodiment, the first material contains polycarbonates, polysulfones, or polypropylenes or is comprised only of these plastics, and/or that the second material contains soft plastics, in particular thermoplastic elastomers such as TPE, PTFE, soft PVC, or silicone, or is completely comprised of these materials.

According to a further example embodiment, a syringe, a carpule, or the like including a distal end 91 and a terminal extension 75 is provided thereon, which has an outer surface 79, a free end 85, and at least one depression 87 introduced at a distance thereto into the outer surface, characterized by one of the attachments described above.

What is claimed is:

1. An attachment for a syringe or a carpule which has a distal end and a terminal extension which includes an outer surface, a free end, and at least one depression introduced into the outer surface at a distance to the free end, the attachment being placeable onto the terminal extension, the attachment comprising:
   an annular base body enclosing a free space, into which the terminal extension is introduced, the annular base body being composed of a first material that is dimensionally stable and a second material that is softer than the dimensionally stable first material and that is deformable, wherein the annular base body includes at least one engagement region, which in a state in which the annular base body is plugged onto the terminal extension engages into the at least one depression,
   wherein along an imaginary circumferential line, the annular base body has first regions including the first material, and second regions including the second material,
   wherein in a state in which it is plugged onto the terminal extension, the second material is molded into the at least one depression,
   wherein the second material is embedded into the first material,
   wherein on a first end, the annular base body includes an annular body, which in a state in which it is applied to the terminal extension embraces an annular region of the terminal extension, and wherein the at least one depression is disposed in the annular region of the terminal extension,
   wherein the annular body includes in a circumferential direction along the imaginary circumferential line segments which form the first regions, and laterally adjacent openings in intermediate spaces between the segments, in which the second material is arranged, and which form the second regions, and
   wherein in the state in which the annular body is applied to the terminal extension, the imaginary circumferential line is located in the region of the at least one depression of the extension.

2. The attachment according to claim 1, wherein the annular base body is a two-component injection molded component comprising the first and second materials.

3. The attachment according to claim 1, wherein the annular base body is composed of the first material, and a circumferential region comprises at least one opening in which the second material is provided, which forms the at least one second region.

4. The attachment according to claim 1, wherein the at least one depression is of an annular design.

5. The attachment according to claim 1, wherein the segments are disposed at a same distance to one another.

6. The attachment according to claim 1, wherein the segments and the openings taper towards the free space.

7. The attachment according to claim 1, at least one segment of the segments includes at least one annularly formed cavity, which preferably contains the second material, wherein the at least one segment comprises a circular arc-shaped wall section, which delimits the at least one annularly formed cavity with respect to the free space, and wall regions emanating from the ends of the wall section, which wall regions laterally delimit the at least one annularly formed cavity, wherein the circular arc-shaped wall section and the wall regions are formed to be resilient so that with a force acting from the free space on the circular arc-shaped wall section, the wall regions are forced laterally outward, and thus the widths measured in the circumferential direction of the laterally adjacent openings are reduced.

8. The attachment according to claim 1, wherein the at least one segment includes an inner surface facing the free space, which preferably comprises two lateral regions adjacent to a central region.

9. The attachment according to claim 1, wherein the at least one segment includes an upper side, and wherein in a region of the upper side facing the free space, a slope is provided on which a wedge is placed.

10. The attachment according to claim 1, wherein the first material contains polycarbonates, polysulfones, or polypropylenes or is comprised only of these plastics, and/or wherein the second material contains soft plastics, in particular thermoplastic elastomers such as TPE, PTFE, soft PVC, or silicone, or is completely composed of these materials.

11. A syringe comprising a distal end and a terminal extension provided thereon, which has an outer surface, a free end, and at least one depression introduced at a distance thereto into the outer surface, and further comprising an attachment according to claim 1.

12. A carpule comprising a distal end and a terminal extension provided thereon, which has an outer surface, a free end, and at least one depression introduced at a distance thereto into the outer surface, and further comprising an attachment according to claim 1.

* * * * *